US00PP27137P3

(12) United States Plant Patent
Van Dijk

(10) Patent No.: US PP27,137 P3
(45) Date of Patent: Sep. 6, 2016

(54) *ANTHURIUM* PLANT NAMED 'ANTHINFAM'

(50) Latin Name: ***Anthurium andreanum* L.**
Varietal Denomination: ANTHINFAM

(71) Applicant: ANTHURA B.V., Bleiswijk (NL)

(72) Inventor: Jan Van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 114 days.

(21) Appl. No.: 14/121,088

(22) Filed: Jul. 29, 2014

(65) Prior Publication Data

US 2016/0037697 P1 Feb. 4, 2016

(51) Int. Cl.
*A01H 5/02* (2006.01)

(52) U.S. Cl.
USPC ..... Plt./365

(58) Field of Classification Search
USPC ..... Plt./365
See application file for complete search history.

(56) References Cited

PUBLICATIONS

Anthura Unlimited in Varieties, *Anthurium* Cut flower & Pot plant culture, retrievd on Jan. 7, 2016, retrieved from the Internet at <http://www.grenethplants.nl/images/brochures/ANTHURIUM.pdf> pp. 1,21 and 45.*
New Plants and Flowers, Two new and two improved cut *anthuriums* May 30, 2014, retrieved from the Internet at <http://www.newplantsandflowers.com/two-new-and-two-improved-cut-anthuriums/> 2 pp.*
Anthura *Anthurium:* Cut flower and pot plant culture, published Nov. 5, 2014, pp. 21 and 45.
EU Community Plant Variety Rights, Official Gazette, 2.2013, Apr. 15, 2013, pp. 28 and 49.
EU Community Plant Variety Rights application No. 20130130, filed Jan. 14, 2013, 7 pp.
Japan Plant Breeder's Rights application No. 29236, filed May 26, 2014, 3 pp.

* cited by examiner

*Primary Examiner* — June Hwu
(74) *Attorney, Agent, or Firm* — Jondle & Associates, P.C.

(57) ABSTRACT

A new and distinct variety of *Anthurium* plant named 'ANTHINFAM' particularly characterized by having green spathes very well suited for cutflower culture, a yellow/white spadix with green tip, little shoot formation, a tall plant habit and dark green healthy foliage, is disclosed.

3 Drawing Sheets

Genus and species: *Anthurium andreanum* L.
Variety denomination: 'ANTHINFAM'.

BACKGROUND OF THE NEW PLANT

The present invention comprises a new and distinct variety of *Anthurium*, botanically known as *Anthurium andreanum* L., and hereinafter referred to by the variety name 'ANTHINFAM'. The new variety originated from a hybridization made in November 2000 in Bleiswijk, The Netherlands. The female parent is a light green *Anthurium* plant designated '1535-02' (unpatented), while the male parent was a cream Anthurium plant designated '00-271' (unpatented).

A single plant was selected in May 2003 and has been asexually reproduced repeatedly by meristem tissue culture in Bleiswijk, The Netherlands over a five-year period. The present invention has been found to retain its distinctive characteristics through successive asexual propagations.

Plant Breeder's Rights for this variety have been applied for in Europe on Jan. 14, 2013. 'ANTHINFAM' has not been made publicly available or sold anywhere in the world more than one year prior to the filing of this application.

SUMMARY OF THE INVENTION

The following are the most outstanding and distinguishing characteristics of this new variety when grown under normal horticultural practices in Bleiswijk, The Netherlands.

1) Green spathes very well suited for cutflower culture;
2) Yellow/white spadix with green tip;
3) Little shoot formation;
4) Tall plant habit; and
5) Dark green healthy foliage.

DESCRIPTION OF THE PHOTOGRAPHS

This new *Anthurium* plant is illustrated by the accompanying photographs which show the overall plant habit including blooms and foliage of the plant; the colors shown are as true as can be reasonably obtained by conventional photographic procedures. The photographs are of a 300-week old plant grown in a greenhouse in Bleiswijk, The Netherlands in 2014.

DESCRIPTION OF THE NEW VARIETY

Figure 1:
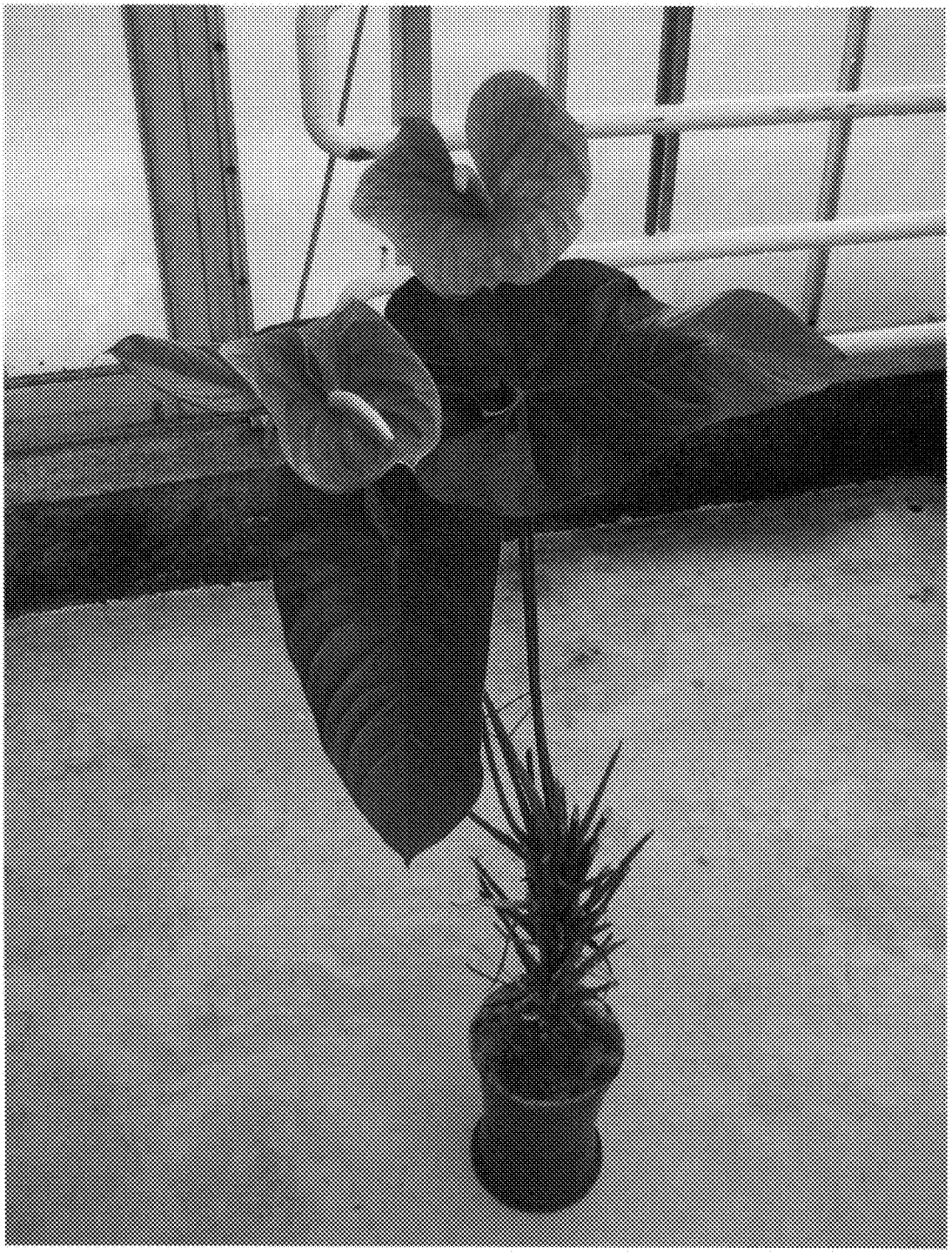
FIG. 1 shows the overall plant habit, including blooms and foliage.
Figure 2:
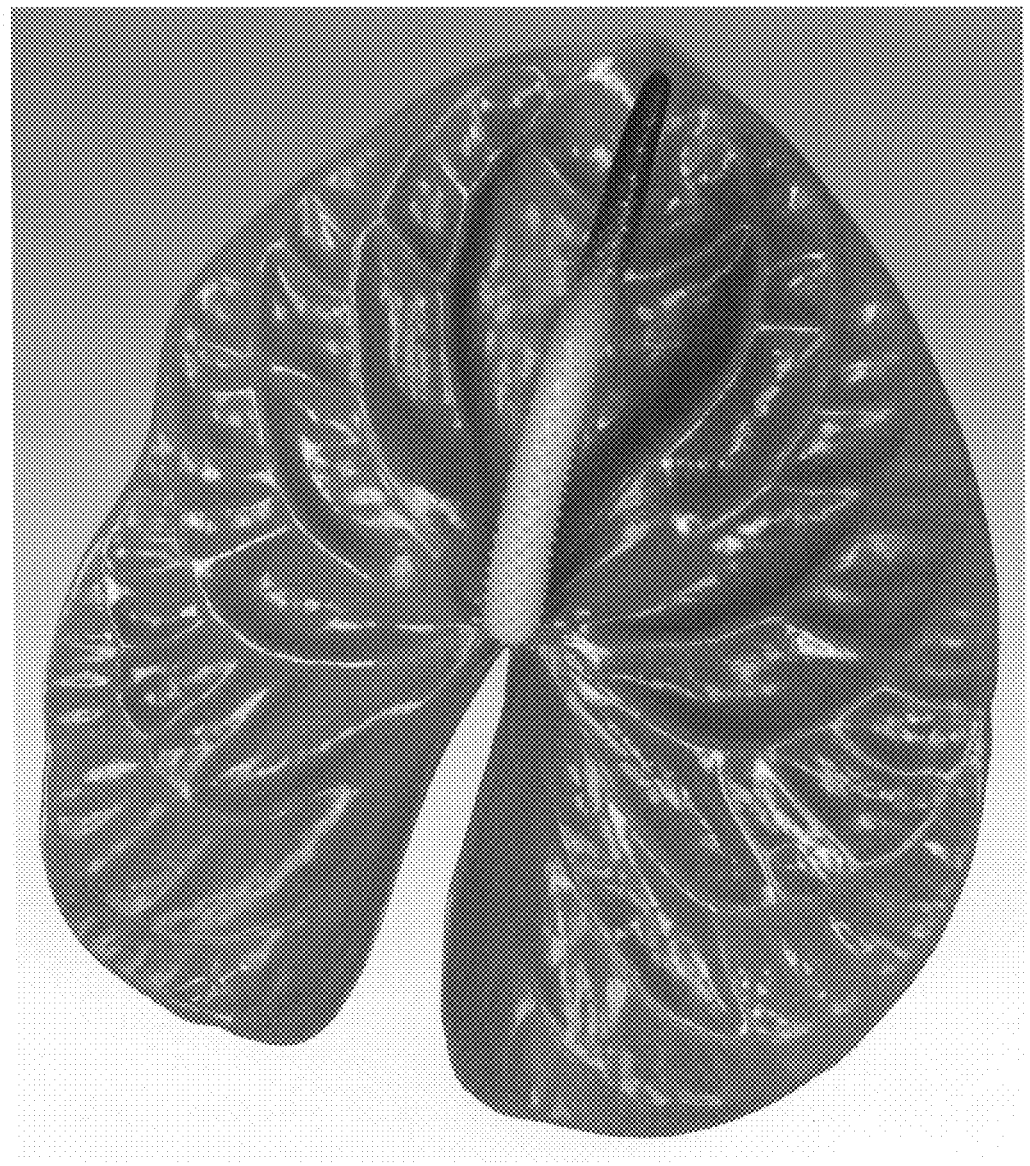
FIG. 2 shows a close-up of the mature spathe. The base of the spadix is mature (yellow/white) and the tip of the spadix is immature (green).
Figure 3:
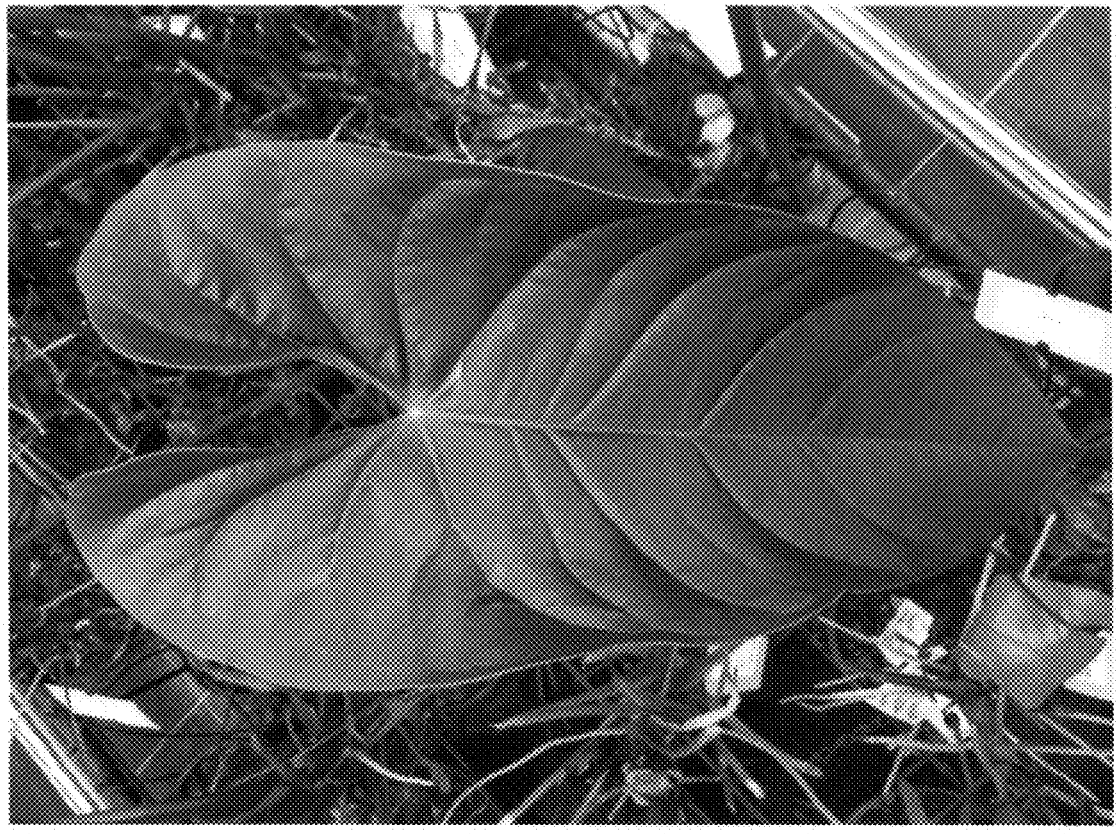
FIG. 3 shows a close-up of the upper surface of the mature leaf.

The following detailed description sets forth the distinctive characteristics of 'ANTHINFAM'. The data which define these characteristics were collected from asexual reproductions carried out in Bleiswijk, The Netherlands. The plant history was taken on 300-week old plants which were planted from tissue culture in 7-centimeter pots and grown in a glass greenhouse between 19° C. and 24° C. Observations were made in February 2014. Color readings were taken under 5000 lux natural light in the greenhouse. Color references are primarily to The R.H.S. Colour Chart of The Royal Horticultural Society of London (R.H.S.) (2001).

DETAILED BOTANICAL DESCRIPTION

Classification:

*Family*.—Araceae.

*Botanical*.—*Anthurium andreanum* L.

*Common name*.—*Anthurium*.

*Demonimation*.—'ANTHINFAM'.

Parentage:

*Female parent*.—*Anthurium* plant '1535-02' (unpatented).

*Male parent*.—*Anthurium* plant '00-271' (unpatented).

Plant:

*Propagation*.—Tissue culture.

*Root description*.—Creamy white-colored roots with hairy lateral roots having yellow-colored root tips.

*Time to produce a finished flowering plant*.—50 to 70 weeks for a full grown, cutflower plant.

*Growth habit*.—Herbaceous perennial.

*Height* (*measured from soil, including inflorescence*).—70.0 cm to 100.0 cm.

*Width* (*measured from leaf tips*).—100.0 cm to 140.0 cm.

Leaves:

*Immature leaves*.—Length: 5.0 cm to 20.0 cm. Width: 3.0 cm to 12.0 cm. Color: Upper surface: RHS 146A. Lower surface: RHS 147B. Texture (both upper and lower surfaces): Shiny flat/no texture.

*Mature leaves*.—Length (fully expanded): 35.0 cm to 45.0 cm. Width: 20.0 cm to 25.0 cm. Shape: Ovate. Apex: Acuminate. Base: Touching. Leaf blade angle with the petiole: Between 90 degrees and 140 degrees. Leaf margin: Entire. Color: Upper surface: RHS 139A. Lower surface: RHS 137C. Texture: Shiny flat to slightly blistered. Venation: The veins protrude at the underside of the leaves. Venation color: Upper surface: RHS 137B. Lower surface: RHS 138B.

*Lobes*.—Arrangement: Free (non-touching). Length of lobes of mature leaf blades: 8.0 cm to 12.0 cm. Width of lobes of mature leaf blades: 8.0 cm to 10.0 cm. Distance from petiole/leaf junction to highest point on lobes of mature leaf blades: 9.0 cm to 13.0 cm.

*Petiole*.—Cross-section: Round. Diameter: 0.5 cm to 0.8 cm. Length: 40.0 cm to 55.0 cm for a mature leaf size. Color: Mature leaf: RHS 138A. Immature leaf: RHS 138B. Cataphyl color surrounding the petiole: Outside: RHS 138A. Inside: RHS 193A.

*Geniculum*.—Length: 1.5 cm. Width: 0.7 cm to 0.8 cm. Color: RHS 138A.

Inflorescence:

*Arrangement*.—Slightly above the leaf canopy.

*Flowering habit* (*length of flowering season*).—Continuous.

*Number of inflorescences per plant*.—5 to 7 per plant per year.

*Fragrance*.—Absent.

*Longevity of inflorescence on plant*.—Over 18 weeks.

*Longevity of the flower as a cut flower*.—40 days to 45 days.

Spathe:

*Buds*.—The spathe is tightly rolled around the spadix and extrudes from the peduncle sheath. After the spathe is fully open the peduncle elongates some extra centimeters.

*Arrangement*.—Spathe angle with the peduncle is between 80 degrees and 100 degrees; the spathe stands on a wiry peduncle about 10 cm to 20 cm above the foliage.

*Shape*.—Broad elliptic.

*Apex*.—Broad acute.

*Base*.—Both free (non-touching) and touching.

*Base shape*.—Cordate.

*Texture*.—Shiny, slightly blistered.

*Margin*.—Entire.

*Size*.—Height: 60.0 cm to 80.0 cm (peduncle length at maturity). Length: 14.0 cm to 18.0 cm. Width: 11.0 cm to 16.0 cm.

*Color*.—Just fully open: Upper surface: RHS 146D. Lower surface: RHS 146D. 1 to 2 weeks after opening (Upper and lower surfaces): RHS 146C. 5 to 8 weeks after opening: Upper surface: RHS 144A. Lower surface: RHS 146C. Depending on cultural circumstances, a pale brownish blush might be present starting at the peduncle or spadix.

Peduncle:

*Shape*.—Wiry.

*Cross-section*.—Round.

*Length*.—60.0 cm to 80.0 cm.

*Diameter*.—0.6 cm to 0.9 cm.

*Color*.—RHS 146B at unrolling of spathe; when the spathe ages on the plant (without cutting the spathe) the color changes slowly to approximately RHS 177A.

Flowering time:

*General*.—One small rooted untreated tissue culture plant of 4 cm tall will flower after 6 to 8 months, depending on the season, and 1 blossom will appear at a time. More blossoms appear successively after every 6 to 10 weeks so that there is a continuous production of cutflowers. Smaller blossoms may occur on less mature plants.

Spadix:

*Size*.—Length: 8.0 cm to 11.0 cm (depending on flower size). Width (at apex): 0.4 cm to 0.5 cm. Width (at base): 0.7 cm to 0.9 cm.

*Shape*.—Columnar.

*Angle from spadix tip to peduncle*.—120 degrees.

*Texture*.—When the spathe is unfurling the spadix is smooth. When the spadix matures, very small stigmata protrude. The stigmata are evenly distributed round the spadix. The spadix matures from base to top, slowly giving the spadix a somewhat coarse appearance.

*Color*.—The spadix becomes mature with time, with the spadix becoming yellow/white from the base to the tip. The distal green part becomes smaller until it changes color completely to yellow/white. Immature: RHS 146C. Mature: RHS 158B. Ages to: RHS 151A.

Flowers:

*Flower bud*.—Length: 9.5 cm to 10.5 cm. Diameter: 1.2 cm to 1.3 cm in the middle; the bud becomes smaller towards the tip. Color: RHS 144B (green).

*Quantity per spadix*.—600 to 900.

*Spadix flower arrangement*.—Bisexual, rounded in cross-section.

*Shape*.—Very small.

*Size*.—Length: 0.1 cm to 0.2 cm. Diameter (maximum): 0.2 cm.

*Color*.—RHS 158B.

Reproductive organs:

*Stamens*.—Anthers and filaments are not clearly visible on the spadix.

*Pollen amount*.—Little pollen production.

*Pollen color*.—RHS 155A.

*Pistil*.—Quantity: 600 to 900 on a mature spadix. Length: Less than 0.01 cm. Color: RHS 158B.

*Style*.—Very small.

*Stigma*.—Shape: Round. Diameter: Less than 0.1 cm. Color: RHS 158B.

*Ovary*.—Ovaries are produced, but are too small to observe.

*Ovary color*.—Not measured/too small.

Fruit and seed set: None observed.

Disease and pest resistance/susceptibility: Not observed to date.

COMPARISON WITH PARENTAL AND COMMERCIAL VARIETIES

'ANTHINFAM' differs from the female parent plant '1535-02' (unpatented) in that 'ANTHINFAM' has green spathes and a yellow/white spadix with a green tip, whereas '1535-02' has light green spathes and a white spadix with a yellow tip.

'ANTHINFAM' differs from male parent plant '00-271' (unpatented) in that 'ANTHINFAM' has green spathes without pink veins, whereas '00-271' has cream white spathes with pink veins. Additionally, 'ANTHINFAM' has a yellow/white spadix with a green tip, whereas '00-271' has a white spadix with an orange tip.

'ANTHINFAM' differs from commercial variety 'Midori' (unpatented) in that 'ANTHINFAM' has a straight sturdy stem, good leaf quality and a relatively short internode length, whereas 'Midori' has a sturdy but curved stem, medium to poor leaf quality and a long internode length.

I claim:

1. A new and distinct variety of *Anthurium* plant named 'ANTHINFAM' as shown and described herein.

* * * * *